(12) United States Patent
Parent et al.

(10) Patent No.: US 10,117,694 B2
(45) Date of Patent: Nov. 6, 2018

(54) BONE SCREW, AND BONE FIXATION SYSTEM AND METHOD

(71) Applicant: Spinologics Inc., Saint Lambert (CA)

(72) Inventors: Stefan Parent, Saint-lambert (CA); Jean-Marc Mac-Thiong, Ville Mount-Royal (CA); Hubert Labelle, Laval (CA); Mark Driscoll, Norte-Dame-de-l'lle-Perrot (CA)

(73) Assignee: Spinologics Inc., Saint-Lambert (CA)

( * ) Notice: Subject to any disclaimer, the term of this patent is extended or adjusted under 35 U.S.C. 154(b) by 0 days.

(21) Appl. No.: 15/845,570

(22) Filed: Dec. 18, 2017

(65) Prior Publication Data

US 2018/0125554 A1    May 10, 2018

Related U.S. Application Data

(63) Continuation of application No. 14/129,376, filed as application No. PCT/CA2012/000625 on Jun. 28, 2012, now Pat. No. 9,861,411.

(60) Provisional application No. 61/502,203, filed on Jun. 28, 2011.

(51) Int. Cl.
| | |
|---|---|
| *A61B 17/04* | (2006.01) |
| *A61B 17/86* | (2006.01) |
| *A61F 2/08* | (2006.01) |
| *A61B 17/68* | (2006.01) |

(Continued)

(52) U.S. Cl.
CPC .......... *A61B 17/8625* (2013.01); *A61B 17/68* (2013.01); *A61B 17/7055* (2013.01); *A61B 17/864* (2013.01); *A61B 17/8645* (2013.01); *A61B 17/88* (2013.01);

(Continued)

(58) Field of Classification Search
CPC combination set(s) only.
See application file for complete search history.

(56) References Cited

U.S. PATENT DOCUMENTS

| | | |
|---|---|---|
| 361,985 A | 4/1887 | Bush |
| 4,773,402 A | 9/1988 | Asher et al. |
| 5,108,397 A | 4/1992 | White |

(Continued)

FOREIGN PATENT DOCUMENTS

| | | |
|---|---|---|
| TR | WO2010107403 A1 | 9/2010 |
| TR | WO2011014135 A3 | 5/2011 |
| WO | WO 2009/044395 | 4/2009 |

OTHER PUBLICATIONS

Extended Search Report for European Application No. 12804588.7, dated Mar. 25, 2014, 11 pages.

(Continued)

*Primary Examiner* — Sameh Boles
(74) *Attorney, Agent, or Firm* — Foley & Lardner LLP

(57) ABSTRACT

A bone screw for pelvic bone fixation, the bone screw comprising an elongate body having a first end which is threaded for engaging at least one bone in the pelvic region, a second end comprising a screw head, and at least one opening across the length of the elongate body for adjustably receiving a fastening means to limit movement of the bone screw away from the engaged bone in use, wherein the at least one opening is shaped such that the position of the fastening means relative to the elongate body of the bone screw can be adjusted. A system for bone fixation in the pelvic region includes the bone screw and the fastening means.

23 Claims, 10 Drawing Sheets

(51) Int. Cl.
*A61B 17/88* (2006.01)
*A61B 17/70* (2006.01)

(52) U.S. Cl.
CPC ....... *A61B 17/8872* (2013.01); *H05K 999/99* (2013.01); *A61B 2017/8655* (2013.01)

(56) References Cited

U.S. PATENT DOCUMENTS

| | | | |
|---|---|---|---|
| 5,127,912 | A | 7/1992 | Ray et al. |
| 5,133,717 | A | 7/1992 | Chopin |
| 5,242,444 | A | 9/1993 | MacMillan |
| 5,306,275 | A | 4/1994 | Bryan |
| 5,498,252 | A | 3/1996 | Bryan |
| 5,527,310 | A | 6/1996 | Cole et al. |
| 5,593,407 | A | 1/1997 | Reis |
| 5,601,554 | A | 2/1997 | Howland et al. |
| 5,643,264 | A | 7/1997 | Sherman et al. |
| 5,733,307 | A | 3/1998 | Dinsdale |
| 5,928,233 | A | 7/1999 | Apfelbaum et al. |
| 6,015,409 | A | 1/2000 | Jackson |
| 6,342,056 | B1 | 1/2002 | Mac-Thiong et al. |
| 6,402,753 | B1 | 6/2002 | Cole et al. |
| 6,409,768 | B1 | 6/2002 | Tepic et al. |
| 6,517,541 | B1 | 2/2003 | Sesic |
| 6,520,990 | B1 | 2/2003 | Ray |
| 6,565,566 | B1 | 5/2003 | Wagner et al. |
| 6,635,059 | B2 | 10/2003 | Randall et al. |
| 6,709,436 | B1 | 3/2004 | Hover et al. |
| 6,808,527 | B2 | 10/2004 | Lower et al. |
| 7,198,627 | B2 | 4/2007 | Bagga |
| 7,763,021 | B2 | 7/2010 | Cole et al. |
| 7,789,895 | B2 | 9/2010 | Heinz |
| 7,850,719 | B2 | 12/2010 | Gournay et al. |
| 7,967,847 | B2 | 6/2011 | Barker et al. |
| 8,052,726 | B2 | 11/2011 | Nayet et al. |
| 3,128,666 | A1 | 3/2012 | Falahee |
| 8,177,785 | B2 | 5/2012 | Vaidya |
| 8,414,582 | B2 | 4/2013 | Overes et al. |
| 8,414,648 | B2 | 4/2013 | Reiley |
| 2003/0065329 | A1 | 4/2003 | Vaughan |
| 2003/0181982 | A1 | 9/2003 | Kuslich |
| 2004/0193157 | A1 | 9/2004 | Falahee |
| 2005/0069397 | A1 | 3/2005 | Shavit et al. |
| 2005/0101958 | A1 | 5/2005 | Adam |
| 2006/0030852 | A1 | 2/2006 | Servain |
| 2006/0111717 | A1 | 5/2006 | Saueressig et al. |
| 2007/0233100 | A1 | 10/2007 | Metzinger |
| 2007/0270848 | A1 | 11/2007 | Lin |
| 2008/0021454 | A1 | 1/2008 | Choa et al. |
| 2008/0021455 | A1 | 1/2008 | Chao et al. |
| 2008/0021456 | A1 | 1/2008 | Gupta et al. |
| 2008/0221577 | A1 | 9/2008 | Elghazaly |
| 2010/0087878 | A1 | 4/2010 | Abdou |
| 2010/0256638 | A1 | 10/2010 | Tyber et al. |
| 2010/0312280 | A1 | 12/2010 | Overes et al. |
| 2011/0034957 | A1 | 2/2011 | Biedermann |
| 2011/0087289 | A1 | 4/2011 | Pham et al. |
| 2011/0282398 | A1 | 11/2011 | Overes et al. |
| 2012/0197254 | A1* | 8/2012 | Wolfe ................ A61B 17/1717 606/62 |

OTHER PUBLICATIONS

Ilharreborde et al., Pelvic ring fractures internal fixation: Iliosacral screws versus sacroiliac hinge fixation, Orthop Traumatol Sura Res Dec. 2009;95(8):563-7.
Sciulli et al., CT-Guided Iliosacral Screw Placement: Technique and Clinical Experience, AJR Am J Roentgenol. Feb. 2007;188(2):W181-92.
Yu et al., Biomechanical advantages of dual over single iliac screws in lumbo-iliac fixation construct, Eur Spine J. Jul. 2010;19(7):1121-8.
Dalstra et al., Load transfer across the pelvic bone., J Biomech. Jun. 1995;28(6):715-24.
Kostuik, Spinopelvic fixation (Review), Neurology India, Dec. 2005, 53(4): 443-8.
Zheng et al., Effect of Iliac Screw Insertion Depth on the Stability and Strength of Lumbo-Iliac Fixation Constructs: Spine (Phila Pa 1976). Jul. 15, 2009;34(16):E565-72.
Rhee et al., Lumbo-sacro-pelvic Fixation Using Iliac Screws for the Complex Lumbo-sacral Fractures, J Korean Neurosurg Soc. Dec. 2007; 42(6): 495-498.
International Search Report and Written Opinion for PCT/CA2012/000625, dated Sep. 4, 2012, 4 pages.

* cited by examiner

BONE SCREW, AND BONE FIXATION SYSTEM AND METHOD

CROSS-REFERENCE TO RELATED APPLICATIONS

The present application is a continuation of U.S. patent application Ser. No. 14/129,376, which has a 371(c) date of Dec. 26, 2013, which is a U.S. National Stage Application claiming the benefit of International Application No. PCT/CA2012/000625, filed on Jun. 28, 2012, which claims priority from U.S. Provisional Patent Application No. 61/502,203, filed Jun. 28, 2011. The entire contents of all 3 applications are incorporated herein by reference in their entirety.

FIELD OF THE INVENTION

The present invention relates to a bone screw, and bone fixation system and method, and more specifically although not exclusively to a bone screw, and bone fixation system and method for the spinal-pelvic region.

BACKGROUND OF THE INVENTION

Spinal-pelvic deformities, trauma, fractures, tumors, inflammation and degeneration can necessitate surgical intervention to secure bones to each other or implants to the bone. Implants such as rods and plates can be used to replace or augment bone. Fixation devices such as hooks, wires, screws and connectors can be used to secure the implants to bone or to connect boney elements together.

In the spinal-pelvic region, bone attachment of implants or fixation devices can be to the spinal column, sacrum bone or ilium bone. Known implants include spinal rods and plates. Fixation devices include iliac screws, sacral screws, and iliac-sacral screws which can be joined together or to spinal rods/plates by a variety of connectors. However, the sacrum has a thin cortical shell often with poor trabecular bone quality which limits screw length selection to the detriment of stable fixation. The ilium offers adequate fixation area but is not sufficient on its own as it may encounter problems of screw pullout and loosening over time. Screw pullout is mainly associated with the presence of a mobile sacro-iliac joint and with an offset distance between iliac screws and an implant placed in the lumbar and/or sacral spine. Moreover, current techniques of attempting to limit the extent of screw pullout have limited success and are surgically complex which can undesirably increase operating times.

Therefore, it is desired to overcome or reduce at least some of the above-described problems.

SUMMARY OF THE INVENTION

The embodiments of the present invention reduce the difficulties and disadvantages of the aforesaid designs and treatments.

Broadly, from one aspect of the present invention, there is provided a bone screw which can engage with bone and which is arranged to be interconnectable with a fastening means in order to limit movement of the bone screw away from the engaged bone in use. One application of the bone screw is in the spinal-pelvic region, such as for joining together the iliac and sacrum bones. The threaded bone screw together with the interconnecting fastening means helps to prevent screw pull out from the engaged bone. The bone screw can also be connected to bones or implants in the spine by connectors.

More specifically, there is provided a bone screw for pelvic bone fixation, the bone screw comprising an elongate body having a first end which is threaded for engaging at least one bone in the pelvic region, a second end comprising a screw head, and at least one opening across the length of the elongate body for adjustably receiving a fastening means to limit movement of the bone screw away from the engaged bone in use, wherein the at least one opening is shaped such that the position of the fastening means relative to the elongate body of the bone screw can be adjusted.

By pelvic bone or pelvic region is meant any individual bone or combination of bones selected from the sacrum, ilium, ischium and pubis. In one embodiment, the bone screw is for sacro-iliac fixation and the threaded first end can engage either one or both of the sacrum or the ilium. Advantageously, adjustable positioning of the fastening means facilitates the cross insertion of the fastening means at different insertion angles. This is particularly important in sacro-iliac fixation as the relative position of the sacrum and the ilium varies between patients. The interconnection of the fastening means and the bone screw can at least limit bone screw pull out from the engaged bone and is therefore particularly advantageous for fixation between the sacrum and the ilium bones due to movement between these bones. The interconnection can also avoid or limit screw failure or loosening. The bone screw of the present invention can also be applied to other bones, joints or moving bone/implant combinations.

The at least one opening is formed through the length of the elongate body and can be substantially transverse or at any angle relative to the long axis of the elongate body. The opening can be of any suitable shape such as oval, circular, hour-glass, oblique, coned, or the like. The opening is also of a suitable size relative to the fastening means to allow the fastening means to be adjustably received in the opening of the bone screw. In one embodiment, the opening is oval shaped and wider than a diameter of the fastening means to allow adjustment of the relative angle of the fastening means and the bone screw. The opening can be formed by drilling through the elongate, at an angle to a long axis of the elongate body. The angle is more than 0° and less than 180°.

By suitable shape is meant any shape which allows the fastening means to be received through the opening such that the position of the fastening means can be adjusted. By position is meant that at least the angle of the fastening means can be adjusted relative to the long axis of the bone screw. The opening may also allow adjustment of the relative height of the fastening means along the elongate body.

The thread can extend from the first end towards the second end of the elongate body along a part or the whole length of the elongate body. In one embodiment, the opening is located on an unthreaded portion of the elongate body but can also be formed on a threaded portion. The opening can be formed at any position along the elongate body. For example, it may be formed closer to the screw head end or to the first end.

The screw head can have an opening formed therein for engagement with a screw driver or similar device having a corresponding driving end. The screw head opening can be of any shape or form suitable for torsional engagement to allow the bone screw to be screwed into a bone, preferably a hexagonally shaped opening. The opening can have a width of about 1 to about 30 mm, preferably about 7 mm, and a height of about 1 to about 50 mm, preferably about 5 mm. The screw head may have the same, larger or smaller diameter of the elongate body, or be flush with the elongate body. In one embodiment, the screw head has a diameter of about 3 to about 35 mm, preferably 12 mm.

The elongate body is preferably of generally constant diameter, although it may also have a variable diameter along its length. For example, the first end may have a smaller diameter or a tip to assist with the screwing into bone or include a modified cross section enabling self-tapping. The bone screw may be about 2 to about 500 mm in length, preferably about 80 mm, and have a diameter of about 1 to about 100 mm, preferably about 8 mm diameter.

The fastening means can be a screw such as a sacral or ilium screw, a nail, a pin, or any other suitable fastener which can be adjustably received in the bone screw opening and which can then be fastened to a bone or an implant. In one embodiment, the fastening means is a sacral screw having a length of about 2 to about 500 mm, preferably about 45 mm, and a diameter of about 1 to about 100 mm, preferably about 4 mm diameter.

In one embodiment, the bone screw is cannulated. By this it is meant that there is a hole or bore extending between the first and second ends for receiving a guide wire to assist in the insertion of the bone screw. The hole can be from about 1 mm to about 50 mm, preferably about 1.5 mm in diameter.

In one embodiment, the elongate body of the bone screw is provided with two openings, spaced apart from one another along the elongate body. The openings can be aligned with one another or off-set to provide a three-dimensional fixation system with the fastening means inserted in use.

The bone screw can be made at least partially from a suitable biocompatible material. Biocompatible materials include, but are not limited to, stainless steel, gold, tantalum, titanium alloys, titanium, cobalt chrome, silver, platinum, shape memory alloys, Nitinol, carbon fiber, collagen fiber, polyethylene, Teflon, Bioglass™, polyurethane, calcium phosphate, hydroxyapatite, polyaryl ether ketone, polyether ether ketone, polyether ketone ketone, PEBA, PEBAX, Birsdboro, polytetrafluoroethylene, polyoxymethylene, and the like, including combinations and composites of the above.

Preferably, there is also provided a securing means for holding the fastening means in a desired position in the at least one opening of the bone screw. The securing means can be a set screw receivable in the bore of the bone screw which bore can be threaded. The fastening means can be clamped by passing the set screw through the bore until it reaches the at least one opening and abuts the fastening means to clamp it in the desired position. Any other clamping means can be used as the securing means such as a pin or a nail used alone or with a clamping mechanism such as a spring.

There can also be provided protrusions extending into the at least one opening. These can be used for guiding the fastening means into the at least one opening and/or for holding the fastening means in the desired position.

Optionally, the bone screw may include a lining material or a packing material in at least a portion of the at least one opening. Advantageously, the lining or packing material can guide, retain or hold the fastening means in the at least one opening. In the case of a packing material substantially filling the opening, such as a polymer or a bone material, the fastening means can be forced through the packing material such as by screwing or force-fitting. The packing material can hold the fastening means in position.

The lining or packing material may also include bone material or any other osteoinductive, osteoconductive or osteogenic material for augmenting fixation of the bone screw at the implant site. The lining or packing material may include a bone extender, bone enhancer, or bone substitute having osteoconductive, osteoinductive, or osteogenic properties. For example, the lining or packing material may include bone material from any source, bone allograft or autograft, demineralized bone matrix, morphogenic protein, collagen, suitable polymers, suitable ceramics, natural coral, coranline hydroxyapatite, suitable composites, hydroxyapatite-tricalcium phosphate, or the like.

Alternatively, the lining or packing material can be a smart material which can change dimensions to hold the fastening means in position when placed in contact with body temperature, body fluid moisture, body fluid ions, or a force. For example, the smart material may expand or change shape when placed in contact with the body to secure the position of the fastening means. Smart materials can include, for example, shape memory alloys which are preconditioned to a particular shape, size or form to which they transform at a certain temperature, moisture, pH, stress, strain or torque.

The opening can also be filled, formed or lined with a soft polymer or the like which can allow penetration by the fastening means and resist the pull out of the fastening means to provide a press-fit interconnection.

At least a portion of the bone screw can have a bioactive coating or be made of a bioactive material. Bioactive materials include bioactive glass, soluble glass, resorbable calcium phosphate, hydroxyapatite, glass-ceramics, to name a few. There may also be included cells, drug molecules, therapeutic agents, particles or the like in the bioactive coating, the bioactive material, the lining material or the packing material. The cells may include those involved in hard and soft tissue generation, regeneration, repair and maintenance, for example mesenchymal stem cells, bone marrow stem cell, osteoblasts, preosteoblasts, fibroblasts, muscle cells and chondrocytes, and the like. Therapeutic agents can include hormones, antimicrobials, anti-rejection agents and the like. The drugs can be any molecules for disease, condition or symptom treatment or control, anti-inflammatory, growth factors, vesicle for release of ions, release of gas, release of nutrients and enzymes. In this way, the bone screw can also be used as a substance carrier or as a delivery vehicle, such as for controlled release of drugs or therapeutic agents.

Part or all of the bone screw can be a smart material which can change dimensions or form when placed in contact with body temperature, body fluid moisture, body fluid ions or a force.

The bone screw may also include a connector which is attachable to the bone screw and to an implant. The connector may be attachable to the screw head of the bone screw and have a pair of upwardly extending flanges defining a slot for receiving an implant in use. The implant may be a spinal rod. The connector and the bone screw can be one-piece, or the connector may be separate to the bone screw and attachable thereto. The connector can be moveable in relation to the bone screw.

In one embodiment, the elongate body is threaded at both the first and second ends. This embodiment is useful for applications where the bone screw spans the left and right side of the ilium. In this embodiment, both the first and second ends can have torsionally engageable screw heads for screwing the bone screw into position.

From another aspect, there is provided a fastening means having an elongate body which is sized and shaped to be adjustably receivable in an opening of a bone screw as described above, for interconnecting with the bone screw to limit movement of the bone screw away from the engaged bone in. One end of the fastening means body is adapted to engage at least one bone in the spinal-pelvic region such as the sacrum or the ilium. The body of the fastening means may be threaded or unthreaded. The fastening means may include a connector which is attachable to the fastening means as well as to an implant such as a spinal rod. The fastening means may be a sacrum screw which may have a butterfly type head to allow fixation to a spinal rod by means of a compression fixture such as a set screw. Other types of connectors are also possible.

The fastening means may be cannulated or fenestrated for receiving guide wire or materials to augment fixation such as bone cement or the like. The fastening means may be made of, or include, any of the lining or packing materials, cells, drug molecules, therapeutic agents, particles or the like, described above for the bone screw.

Advantageously, the fastening means may be adapted to mechanically fail (e.g. break) at a force lower than that required to pull out the fastening means, the bone screw, or the assembled bone screw and fastening means from the engaged bone in use. Advantageously, this can facilitate revision surgeries involving removal or repositioning of the bone screw by allowing the removal of the fastening means and/or the bone screw whilst reducing damage to the surrounding bone. In this respect, the fastening means may be sized, shaped or be made of a material with appropriate properties to achieve this. An appropriate geometrical shape may include a narrower portion of the body at which point mechanical failure can occur, or a thinned portion of the body. Alternatively, the fastening means may have variable properties along its length as to enable the controlled failure. These properties include but are not limited to mechanical properties, density, porosity, brittleness, and any number of microscopic or macroscopic irregularities. By means of the mechanical property or geometrical shape of the fastening means, controlled failure of the fastening means outside of normal operation can be achieved which can allow removal or repositioning of the bone screw whilst substantially maintaining bone mass in the surrounding area. In other words, in use, the fastening means can improve the resistance to pull out of the bone screw from a bone to which the bone screw is fixed whilst also having the ability to allow bone screw pull out by its controlled failure if required.

From a further aspect, there is provided a bone fixation system for the pelvic region, the system comprising a bone screw, as described above, and a fastening means, as also described above, which is adjustably receivable in the at least one opening of the bone screw.

Specifically, the bone screw comprises an elongate body having a first end which is threaded for engaging at least one bone in the pelvic region (such as one or both of a sacrum and an ilium bone), a second end comprising a screw head, and at least one opening through the elongate body; and the fastening means has an elongate body with one end adapted to engage at least one bone in the pelvic region (such as the sacrum or the ilium bone), the elongate body being sized to be adjustably receivable in the at least one opening for interconnecting with the bone screw to limit movement of the bone screw away from the engaged bone in use, wherein the at least one opening of the bone screw is shaped such that the position of the fastening means relative to the elongate body of the bone screw can be adjusted. The fastening means can be a sacral screw, an ilium screw, a nail, a pin or an implant. The fastening means can be cannulated or fenestrated. In the case of a fenestrated fastening means, bone cement or the like can be placed, such as by injection, into the openings to augment fixation in situ. The fastening means can be threaded or unthreaded. The fastening means can be sized or shaped to mechanically fail at a lower force than that required to pull out the fastening means from an engaged bone in use.

From another aspect, there is provided a bone fixation method for the pelvic region, the method comprising providing a bone screw comprising an elongate body having a first end which is threaded for engaging a bone in the pelvic region, a second end comprising a screw head, and at least one opening across the length of the elongate body for adjustably receiving a fastening means; attaching the bone screw to the bone in the pelvic region; passing the fastening means through the opening of the bone screw and adjusting the position of the fastening means relative to the bone screw; attaching the fastening means to the same or a different bone in the pelvic region, wherein the attaching can occur before or after passing the fastening means through the opening of the bone screw. The method can be performed percutaneously or through open surgery. The bone screw can be attached to one or both of the sacrum or the ilium, and the fastening means can be attached to the sacrum or the ilium.

The fastening means can be passed through the bone screw opening before or after attaching the bone screw to the bone. The method can further comprise securing the position of the fastening means relative to the bone screw using a securing means. A bioactive material, such as bone cement, can be injected into an opening at one of the ends of the cannulated fastening means or the cannulated bone screw. This can assist with the fixation of the system in situ. Injection of bone cement into a fenestration of the fastening means or the bone screw can also augment fixation in situ.

From a yet further aspect, there is provided use of a bone screw as defined above, a fastening means as described above, or a bone fixation system as defined above, in the spinal and pelvic regions of a human or animal. The use can be for the treatment of spinal or pelvic deformity, imbalance, trauma, tumours, inflammation or degeneration. More specifically, the use can include fixation of the iliac and sacrum bones together, as well as other joints or bone/implants. Advantageously, the bone screw can engage with one or both of the ilium and the sacrum, and the fastening means can engage with one or both of the ilium and sacrum. Specific uses include the treatment of spinal deformity, spondylolisthesis, spinal-pelvic imbalance, spinal-pelvic trauma, fractures, tumors, inflammation and degeneration.

In one embodiment, the sacrum and/or sacroiliac joint may be secured with the bone screw extending from the iliac through to the sacrum with the fastening means being inserted through the sacrum and into the bone screw opening near the bone screw first end in the sacrum. In another embodiment, the sacrum and/or sacroiliac joint may be secured with the bone screw extending from the iliac through to the sacrum and stabilized using a sacral screw extending through the bone screw opening near the screw end in the ilium. In another embodiment, a bone screw which is threaded on both ends is inserted from one side of the ilium to the other through the sacrum, or distally of the sacrum. Interlocking sacrum screws are inserted through two substantially transverse openings in the bone screw body into the sacrum.

In another embodiment, the bone screw may be an iliac screw cross drilled in order to form the opening and stabilized by the cross insertion of another ilium screw that does not cross the ilium but interconnects with the longer iliac screw. Other combinations of cross drilled screws for enhanced stability of any spinal-pelvic fixation devices are possible under the principles of the invention described herein.

From another aspect of the present invention, there is provided a kit for sacra-iliac fixation including at least one bone screw as described above and a fastening means as described above, wherein the bone screw and/or the fastening means have different diameters and/or lengths of different sizes. The kit may also include a guidewire or a tool for insertion of the bone screw and/or the fastening means.

From a yet further aspect, there is provided a tool for assisting in the positioning of the bone screw in situ. The tool can identify the site of bone screw penetration into a bone in the pelvic region such as the sacrum or ilium. The tool can align the openings for the substantially perpendicular insertion of the inter-locking fastening means and to inform the user of their location. The tool comprises a first arm including a first opening formed therethrough for guiding the bone screw, and a second arm including a second opening formed therethrough for guiding the fastening means, wherein the first and second openings have first and second axis respectively which form an angle of more than zero and less than 180°. The first and second arms may be spaced from one another, or moveable with respect to each other to vary the angles.

BRIEF DESCRIPTION OF THE DRAWINGS

Further aspects and advantages of the present invention will become better understood with reference to the description in association with the following in which.

DETAILED DESCRIPTION OF THE INVENTION

Figure 1:
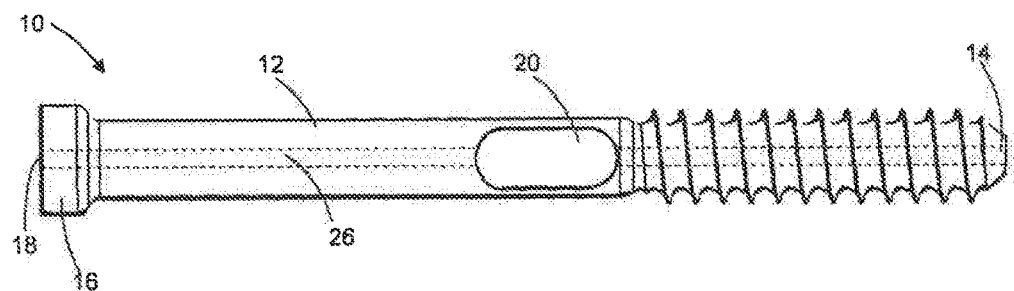
FIG. 1 is a side view of a bone screw with a single opening formed therethrough according to an embodiment of the present invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

Broadly, embodiments of the invention relate to a bone screw which can engage with bone and which is arranged to be interconnectable with a fastening means in order to limit movement of the bone screw away from the engaged bone in use. One application of an embodiment of the present invention, which is described below, is for sacro-iliac fixation in the pelvic region in which bone screw pull-out is a recognized problem due to movement between these bones. However, embodiments of the present invention are also applicable to other bones and bone/implant combinations, particularly bones of a joint in which bone screw pull-out can be of concern.

Figure 2:
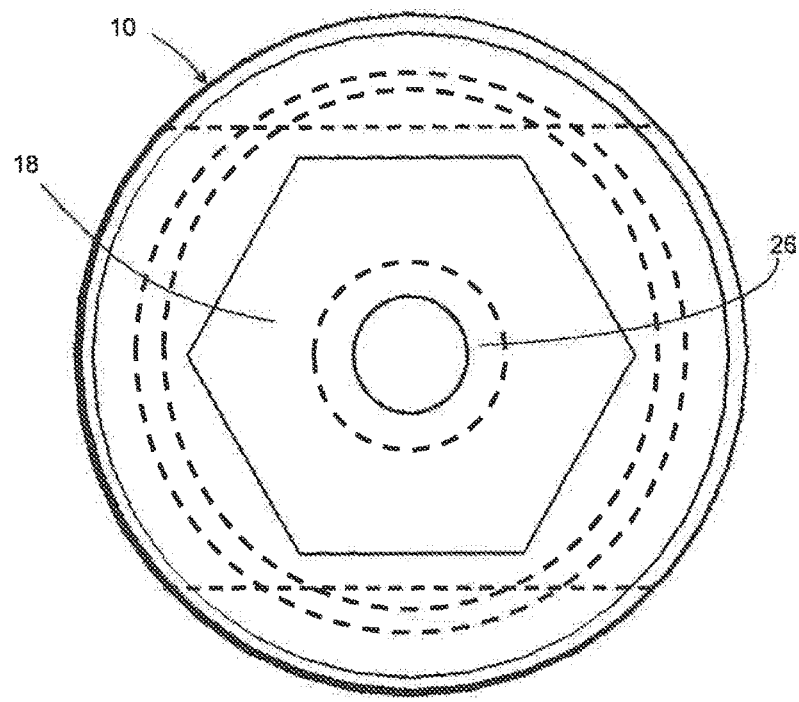
FIG. 2 is an end view of the bone screw of FIG. 1.
Figure 3:
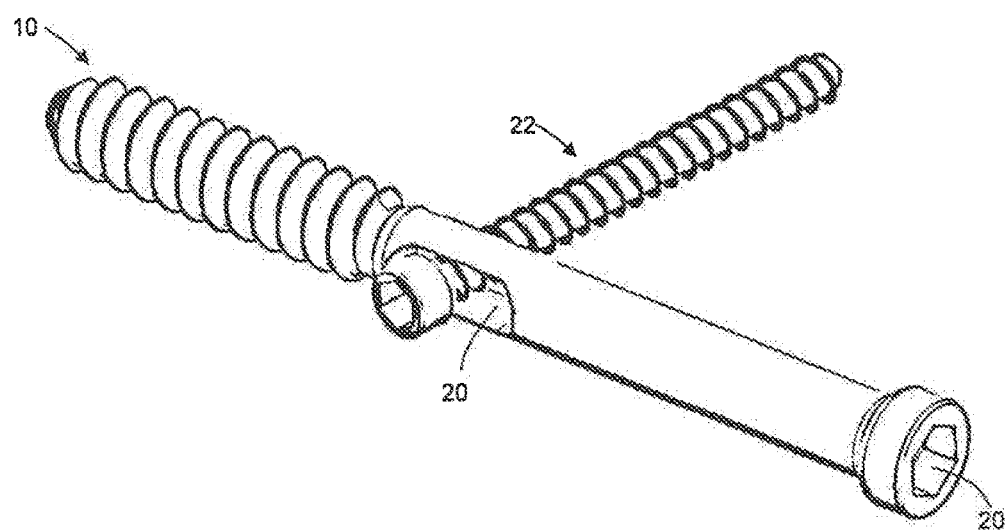
FIG. 3 is an isometric view of the bone screw of FIG. 1 assembled with a fastening means according to another embodiment of the present invention.

Referring now to FIGS. 1 to 3, there is provided a bone screw 10 for sacro-iliac fixation, the bone screw 10 comprising an elongate body 12 having a first end 14 which is threaded for engaging one or both of a sacrum or ilium bone, a second end 16 including a screw head 18, and at least one opening 20 across the length of the elongate body 12 for adjustably receiving a fastening means 22 to limit movement of the bone screw 10 away from the engaged bone in use, wherein the at least one opening 20 is shaped such that the position of the fastening means 22 relative to the elongate body 12 of the bone screw 10 can be adjusted.

In the embodiment of FIG. 1, the opening 20 is located on an unthreaded portion of the elongate body 12 and is formed at substantially 90° to the long axis of the elongate body 12. The opening 20 is oval shaped and wider than a diameter of the fastening means 22, which is a sacral screw, to allow adjustment of the relative position of the fastening means 22 and the bone screw 10. By this it is meant that the angle of the sacral screw, or other fastening means, can be adjusted relative to the long axis of the elongate body 12 of the bone screw 10, as well as the relative height of the sacral screw along the elongate body 12.

The screw head 18 is illustrated in FIG. 2 as being hexagonal for engagement with a screw driver or similar device having a corresponding driving end. However, the screw head 18 can be of any shape or form suitable for torsional engagement to allow the bone screw 10 to be screwed into a bone.

FIG. 3 illustrates the bone screw 10 assembled with the fastening means 22 which forms a bone fixation system 24 of the present invention. The elongate body 12 of the bone screw 10 as illustrated in FIGS. 1-3 has a generally constant diameter. In this embodiment, the bone screw 10 is about 80 mm long and has a diameter of about 8 mm. The bone screw 10 is cannulated, having a bore 26 of about 1.5 mm diameter extending between the first 14 and second ends 16 of the elongate body 12.

Figure 4:
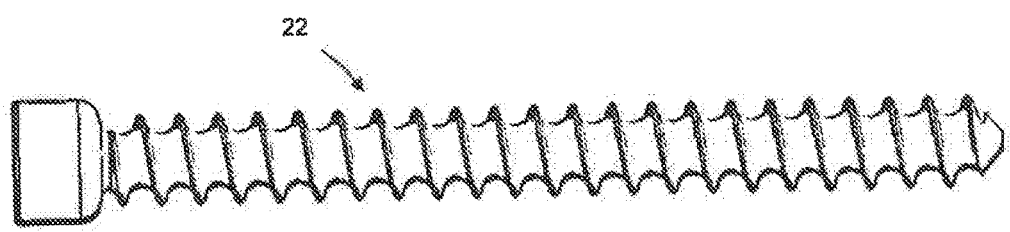
FIG. 4 is a side view of the fastening means of FIG. 3.
Figure 5:
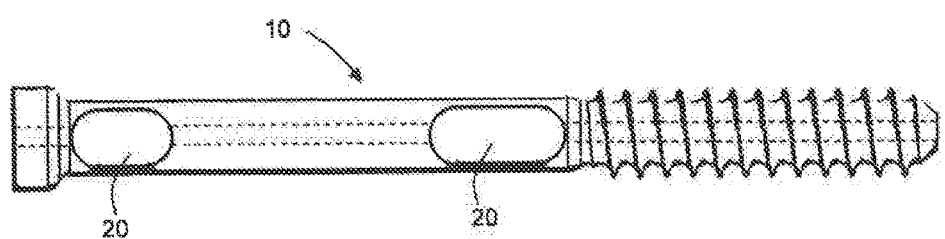
FIG. 5 is a side view of another embodiment of the bone screw of FIG. 1 having two openings formed therethrough.
Figure 6:
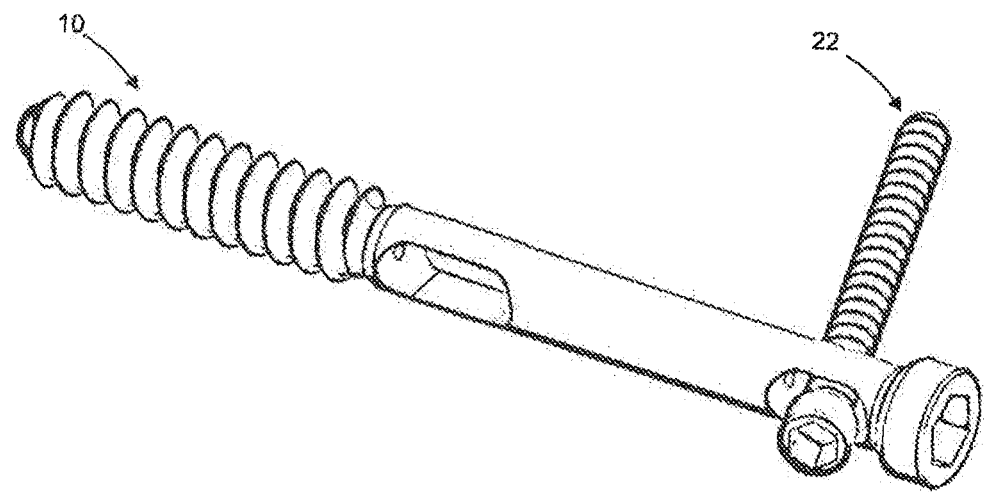
FIG. 6 is an isometric view of the bone screw of FIG. 5 assembled with a fastening means according to an embodiment of the present invention.
Figure 7:
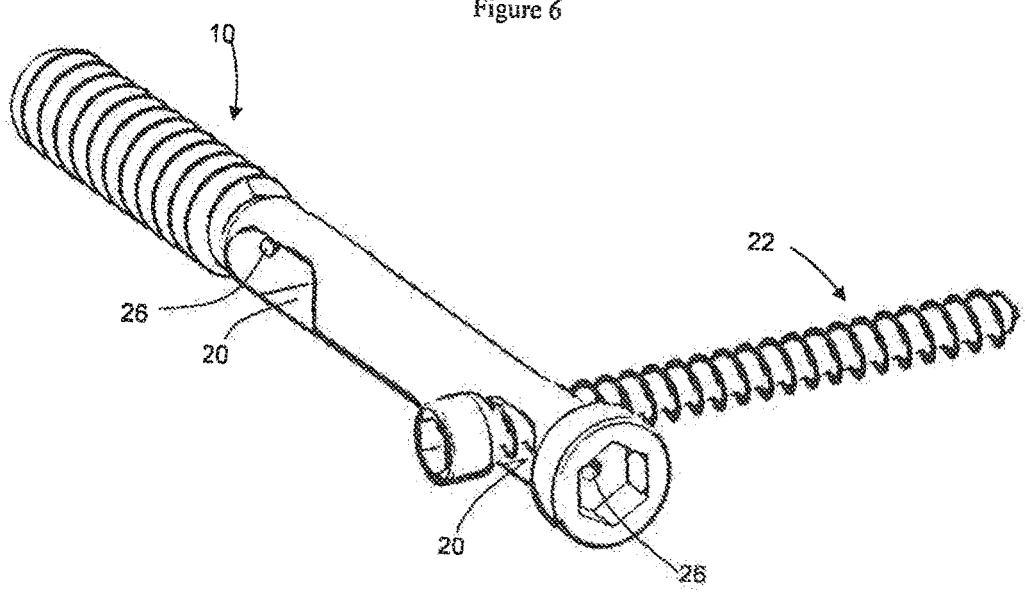
FIG. 7 is the isometric view of FIG. 6 with the fastening means inserted through the opening of the bone screw at a different angle.
Figure 8:
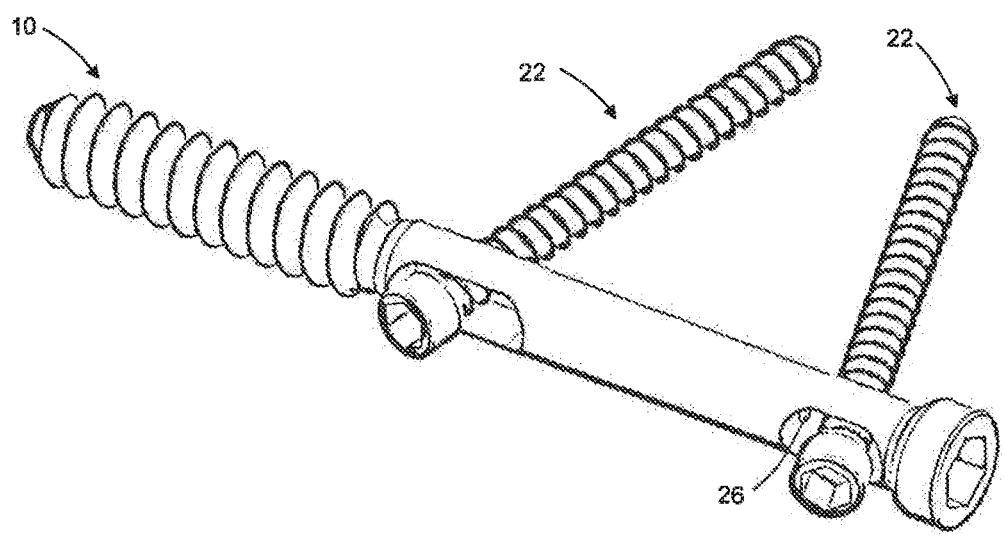
FIG. 8 is an isometric view of the bone screw of FIG. 5 assembled with two fastening means according to another embodiment of the present invention.

The sacral screw illustrated in FIG. 4 is one example of the fastening means 22 which can be interconnected to the bone screw 10. It will be apparent to skilled persons that other types of screws, nails, pins or implants can also be used as the interconnecting fastening means 22, as long as they are dimensioned to be receivable through the opening 20 of the bone screw 10, and can be adjusted within the opening 20 to change their position relative to the bone screw 10.

FIGS. 5 to 8 illustrate another embodiment of the bone screw 10, which differs from that of FIG. 1 in that two openings 20 are provided across the long axis of the elongate body 12. In this embodiment, the openings 20 have the same orientation to each other, although the relative orientations may be different. In use, each of the openings 20 will receive a fastening means 22.

Figure 9:
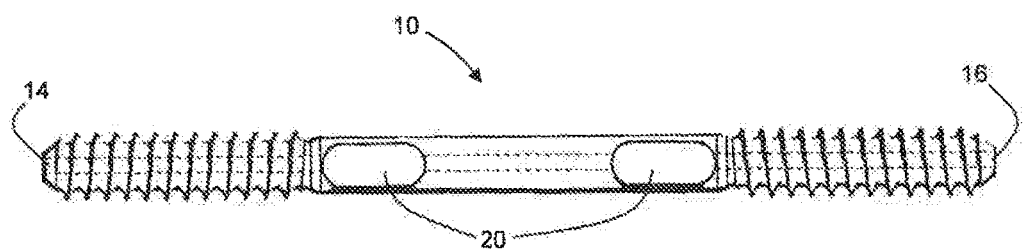
FIG. 9 is a side view of a bone screw of a further embodiment of FIG. 5.
Figure 10:
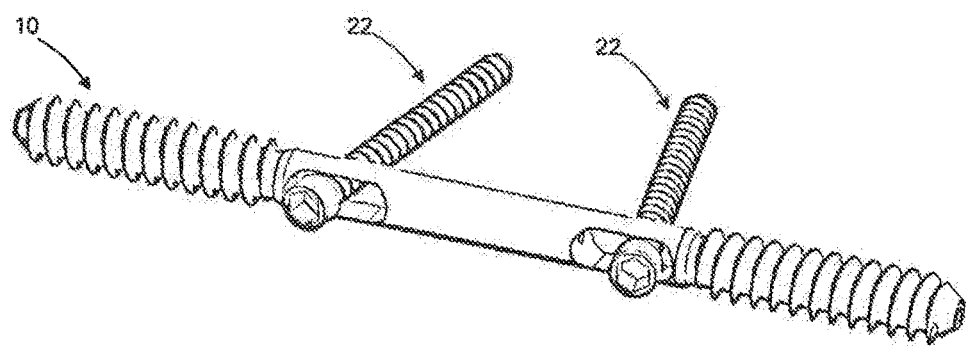
FIG. 10 is an isometric view of the bone screw of FIG. 9 assembled with two fastening means.

The embodiment of FIGS. 9 and 10 differ from those of FIGS. 5 to 8 in that the bone screw 10 is threaded at both ends 14, 16. In this embodiment, both the first and second ends 14, 16 have a screw head 18. This embodiment of the bone screw 10 is useful for trans-iliac fixation, with the bone screw 10 either extending through the sacrum or distally of the sacrum.

Figure 11:
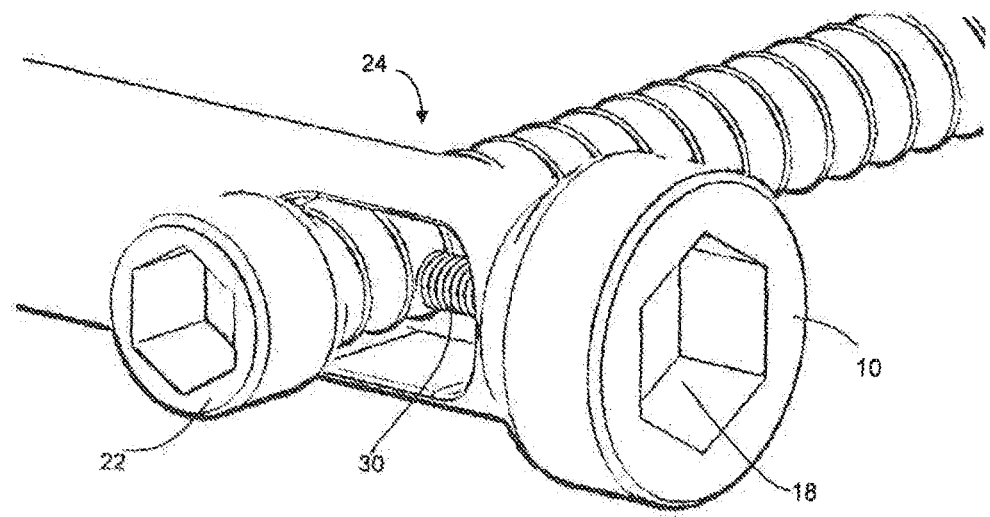
FIG. 11 is a close-up view of a securing means for holding in place a fastening means to a bone screw according to an embodiment of the present invention.

The bone screw 10 can also include a securing means 28 for holding the fastening means 22 in a desired position in the opening 20 of the bone screw 10. In one embodiment, best seen in FIG. 11, the bore 26 of the bone screw 10 is threaded, and there is provided a set screw 30 for being received in the bore 26 and which can be used to extend into the opening 20 and abut the fastening means 22 to clamp it in position.

In a further embodiment (not shown), the opening 20 can be lined with or at least include a lining material or a packing material for guiding the fastening means 22 or for retaining the fastening means 22 in position. The packing material can be a bone material which can augment fixation of the fastening means in position.

In another embodiment (not shown), the packing or lining material, or at least a portion of the bone screw 10, is a smart material which can change dimensions to hold the fastening means 22 in position when placed in contact with body temperature, body fluid moisture, body fluid ions or a force.

Figure 12:
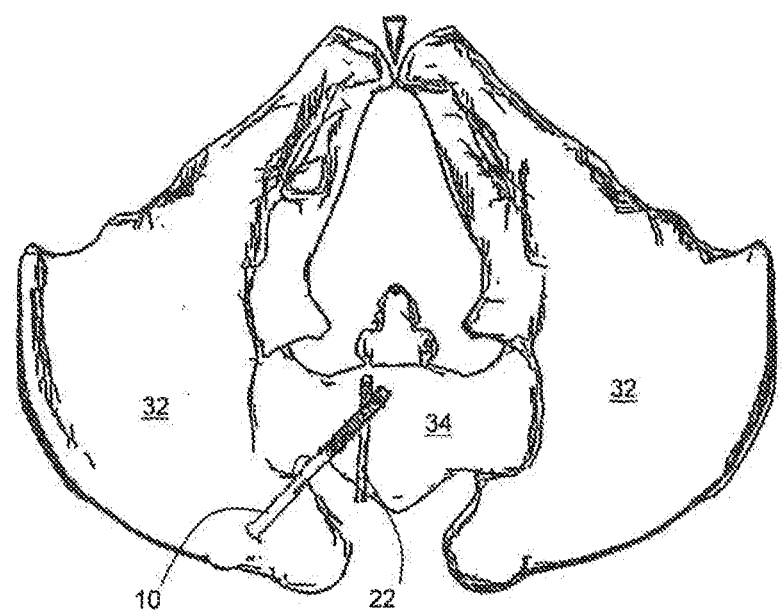
FIG. 12 illustrates a use of embodiments of the bone screw of the present invention in ilium and sacral bones, with a transparency given to the sacrum, ilium, pubis, and ischium for ease of viewing.
Figure 13:
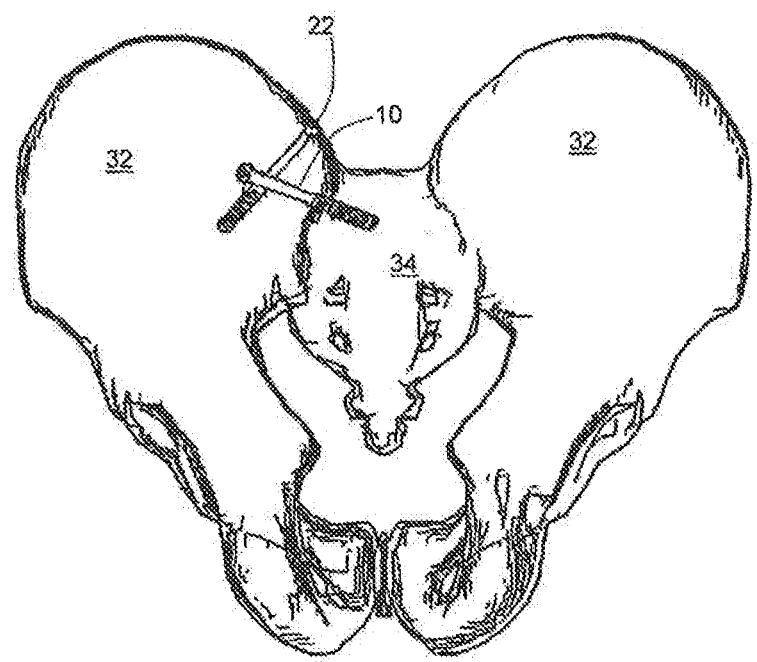
FIG. 13 is a coronal view of FIG. 12.

Referring now to FIGS. 12 and 13, there is shown one use of an embodiment of the bone screw 10. The bone screw 10 extends through the ilium 32 and into the sacrum 34, with the fastening means 22 (a sacral screw) inserted into the sacrum 34 and through the bone screw opening 20. A degree of freedom may exist between the bone screw 10 and the fastening means 22 due to the shape and size of the opening 20. The bone screw 10 has a portion of its elongate body 12 that is not included in bone to which portion can be attached a connector (not shown) which could then be connected to a spinal rod, bone plate or other implant. The connector can be a butterfly type connector.

Figure 14:
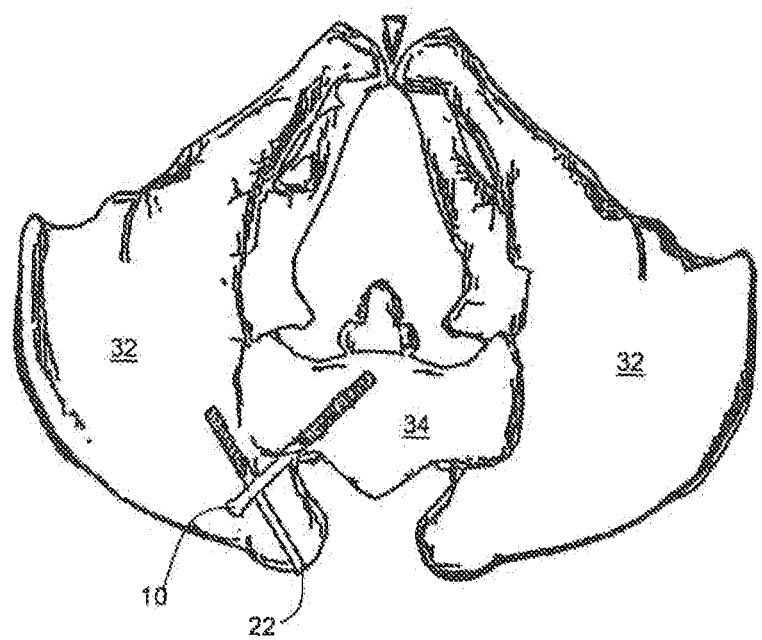
FIG. 14 illustrates another use of embodiments of the bone screw of the present invention in ilium and sacral bones, with a transparency given to the sacrum, ilium, pubis, and ischium for ease of viewing.
Figure 15:
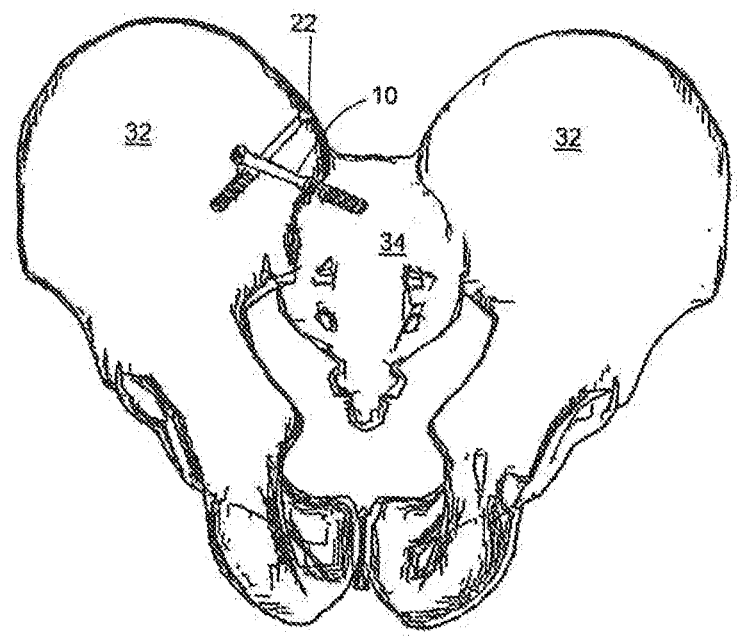
FIG. 15 is a coronal view of FIG. 14.

In FIGS. 14 and 15, the bone screw 10 extends through the ilium 32 and into the sacrum 34. The fastening means 22, which is an iliac screw, is inserted into the ilium 32 and crosses through the bone screw 10.

Figure 16:
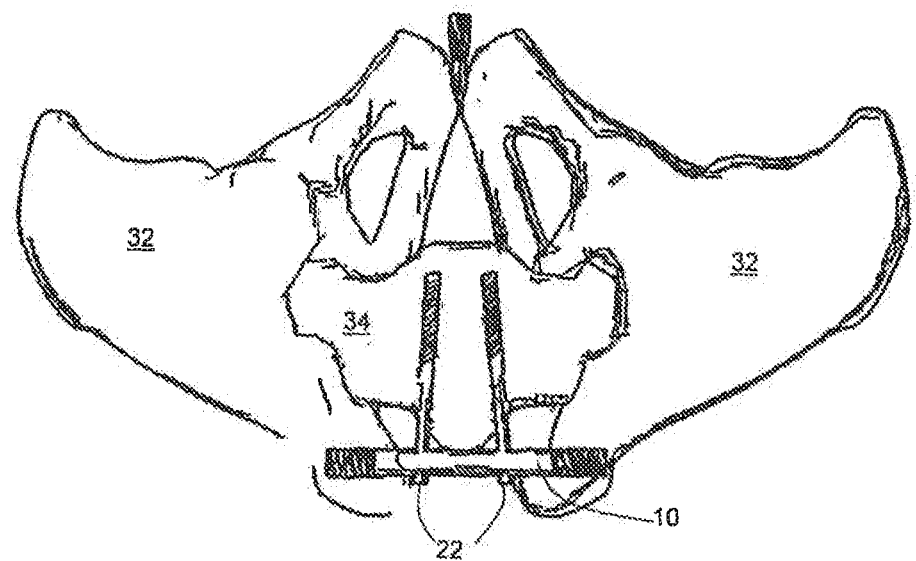
FIG. 16 illustrates yet another use of embodiments of the bone screw of the present invention in ilium and sacral bones, with a transparency given to the sacrum, ilium, pubis, and ischium for ease of viewing.
Figure 17:
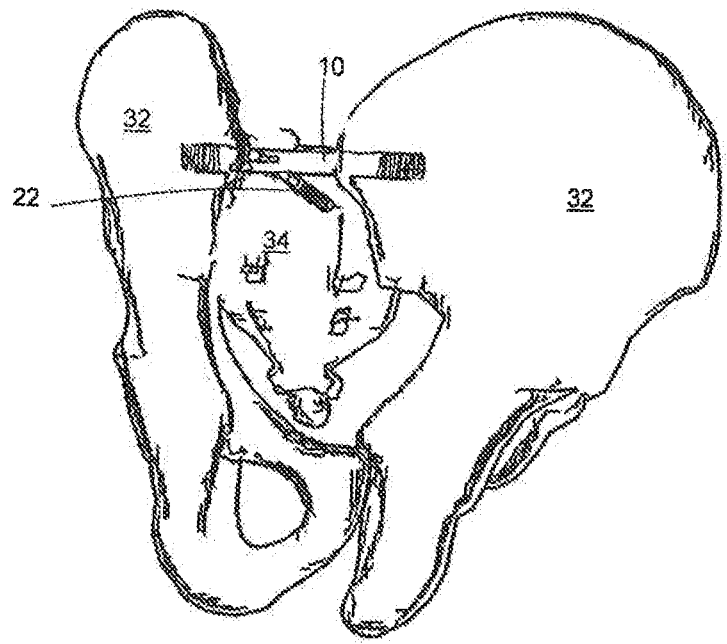
FIG. 17 is an isometric view of FIG. 16.

In FIGS. 16 and 17, the bone screw 10 is similar to a trans-iliac screw having a thread on both ends 14, 16 and two openings 20 formed therethrough. The bone screw 10 extends between the left and right ilium 32 of a patient, in use. One end of the bone screw (for example an entry end) may have threads with a smaller circumference (tighter or more closely spaced) compared to the other end (a trailing end) to improve fixation between the bone screw 10 and the ilia 32. Bolt and nut type fixations (not shown) may also be used to secure the bone screw 10. Once secured in both ilia 32, the bone screw 10 can receive the cross insertion of two fastening means 22, in this embodiment, sacral screws. This procedure may be performed percutaneously, although standard open surgical practices may also be employed. This assembly 24 may also be fixed to spinal rods via connectors (not shown) attached to or forming part of the bone screw 10 or the fastening means 22.

Figure 18:
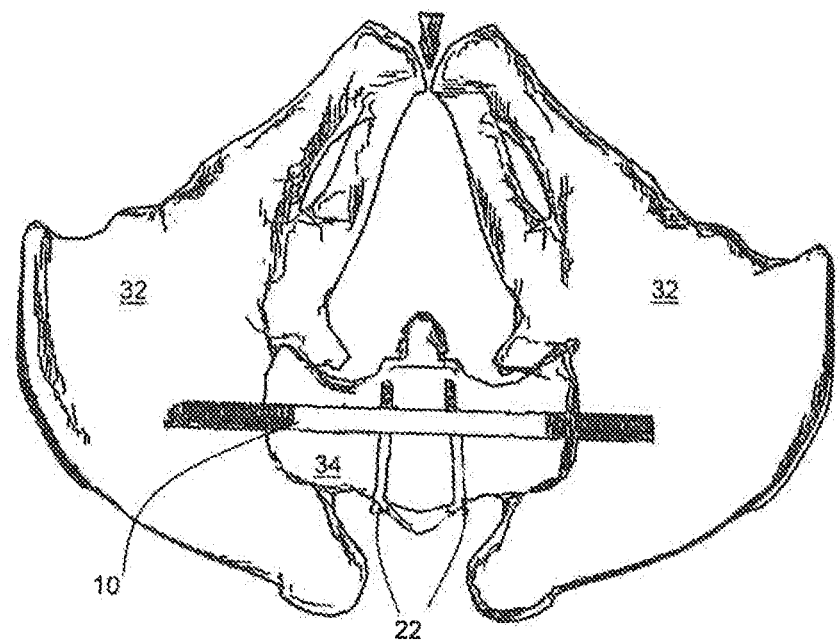
FIG. 18 illustrates a further use of embodiments of the bone screw of the present invention in ilium and sacral bones, with a transparency given to the sacrum, ilium, pubis, and ischium for ease of viewing.

In the embodiment of FIG. 18, the bone screw 10 extends from one ilium 32, through the sacrum 34, and into the other ilium 32. All or selected portions of the bone screw 10 may be threaded to enhance bone fixation. Bolt and nut type fixations (not shown) may also be used to secure the bone screw 10. Once secured in both the ilia 32 and the sacrum 34, the bone screw 10 can receive the cross insertion of two fastening means 22, in this embodiment, sacral screws. This assembly 24 may also be fixed to spinal rods via connectors (not shown) attached to or forming part of the bone screw 10 or the fastening means 22.

Figure 19:
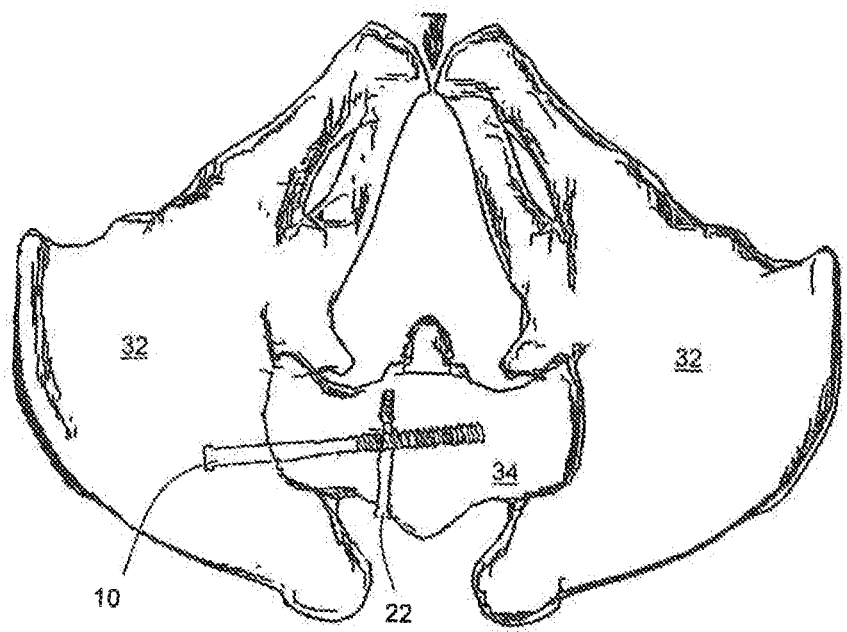
FIG. 19 illustrates a yet further use of embodiments of the bone screw of the present invention in ilium and sacral bones, with a transparency given to the sacrum, ilium, pubis, and ischium for ease of viewing.

FIG. 19 illustrates a further use of the bone screw 10 in which the bone screw 10 extends through the ilium 32 and into the sacrum 34 and spans the sacro-iliac joint, with the fastening means 22 (such as a sacral screw) inserted through the opening 20 and into the sacrum 34, The bone screw 10 is inserted and fixed into both the ilia 32 and the sacrum 34. This insertion path may take place at the level of S1 or S2. The fastening means 22 is a sacral screw. If desired, this assembly 24 may be fixed to spinal rods by means of connectors (not shown).

In use, the bone screw 10 is attached to one or both of the sacrum 34 and the ilium 32 bones, the fastening means 22 is passed through the at least one opening of the bone screw 10 and the relative positions of the fastening means 22 relative to the bone screw 10 adjusted. The fastening means 22 is then attached to the sacrum 34 or the ilium 32 bones, wherein the attaching can occur before or after passing the fastening means 22 through the opening 20 of the bone screw 10. The method can be performed percutaneously or through open surgery. The fastening means 22 can be passed through the bone screw opening 20 before or after attaching the bone screw 10 to the bone. The method can further comprise securing the position of the fastening means 22 relative to the bone screw 10 using a securing means 28. A bioactive material, such as bone cement, can be injected into an opening at one of the ends of the cannulated fastening means or the cannulated bone screw. This can assist with the fixation of the system in situ. Injection of bone cement into a fenestration of the fastening means or the bone screw can also augment fixation in situ.

Figure 20:
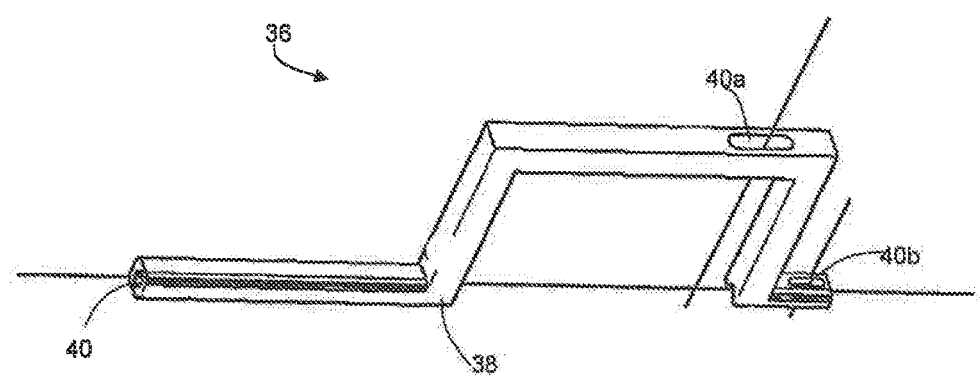
FIG. 20 is a tool for use with embodiments of the bone screw of the present invention.

Reference is now made to FIG. 20 which illustrates a tool 36 for assisting in the insertion of the invention described herein. The tool 36 comprises an elongate body 38 having openings 40 formed therein for guiding the bone screw 10 and the fastening means 22. The openings 40 are at different angles to one another which coincide with the angle of the bone screw opening 20 to the bone screw elongate body 12. Portions of the tool elongate body 38 may be raised in order to provide spacing for a patient's buttocks. For example, in the tool 36 illustrated in FIG. 20, the bone screw 10 is guided through the opening 40a and the fastening means through the opening 40b. The various portions of the tool 36 may be moveable in relation to one another in order to provide further respective angles, i.e. using hinged arms.

It should be appreciated that the invention is not limited to the particular embodiments described and illustrated but includes all modifications and variations falling within the scope of the invention as defined in the appended claims.

What is claimed is:

1. A bone screw for pelvic bone fixation, the bone screw comprising an elongate body having:
    a first end which is threaded for engaging at least one bone in the pelvic region,
    a second end comprising a screw head, and
    at least one opening across the length of the elongate body for adjustably receiving a fastener to limit movement of the bone screw away from the engaged bone in use, wherein the at least one opening is shaped such that the position of the fastener relative to the elongate body of the bone screw can be adjusted,
    wherein the at least one opening provides a truncated geometry and wherein the truncated geometry is symmetrical from the center of the opening.

2. A bone screw according to claim 1, wherein the at least one opening is wider than a diameter of the fastener to allow adjustment of the relative angle of the fastener and the bone screw.

3. A bone screw according to claim 1, further comprising a securing mechanism for holding the fastener in a desired position in the at least one opening of the bone screw.

4. A bone screw according to claim 3, wherein the securing mechanism includes a bore extending from the screw head to the at least one opening, through which bore a clamping mechanism can be passed to abut the fastener to hold it in position.

5. A bone screw according to claim 4, wherein the bore is threaded and wherein the clamping mechanism is a set screw receivable in the threaded bore.

6. A bone screw according to claim 4, wherein the securing mechanism includes protrusions extending into the at least one opening for guiding the fastener into the at least one opening and holding the fastener in the desired position.

7. A bone screw according to claim 1, further including a lining material or packing material in at least a portion of the at least one opening.

8. A bone screw according to claim 7, wherein the packing material is at least one of a bone material packed into the at least one opening and a smart material which can change dimensions to hold the fastener in position when placed in contact with body temperature, body fluid moisture, body fluid ions or a force.

9. A bone screw according to claim 1, further including a connector which is attachable to the bone screw and to an implant, wherein the connector is attachable to the screw head and has a pair of upwardly extending flanges defining a slot for receiving an implant in use.

10. A bone screw according to claim 9, wherein the connector and the bone screw are one-piece.

11. A bone screw according to claim 1, wherein the elongate body is threaded at both the first and second ends.

12. A bone screw according to claim 1, further including a longitudinal opening extending the length of the elongate body for receiving a guide wire.

13. A bone screw according to claim 1, wherein at least a portion of the bone screw has a bioactive coating or is made of a bioactive material or is a smart material which can change dimensions when placed in contact with body temperature, body fluid moisture, body fluid ions or a force.

14. A bone screw according to claim 1, wherein the truncated geometry has an hour-glass geometry, a truncated wedge geometry or a truncated cone geometry.

15. A bone screw according to claim 1, wherein the at least one opening further comprises protrusions extending thereinto for guiding a fastener.

16. A bone screw according to claim 1, wherein a second opening of the two openings provides a second truncated geometry, symmetrical from the center of the second opening, the first truncated geometry and the second truncated geometry being different.

17. A bone fixation method for the pelvic region, comprising
    providing a bone screw comprising an elongate body having a first end which is threaded for engaging at least one bone in the pelvic region, a second end comprising a screw head, and an opening across the length of the elongate body for adjustably receiving a fastener, wherein the opening provides a truncated geometry and wherein the truncated geometry is symmetrical from the center of the opening;
    attaching the bone screw to the at least one bone;
    passing the fastener through the opening of the bone screw and adjusting the position of the fastener relative to the bone screw;
    attaching the fastener to the same or different bone in the pelvic region, wherein the attaching can occur before or after passing the fastener through the opening of the bone screw.

18. A bone fixation method according to claim 17, wherein the fastener can be passed through the bone screw opening before or after attaching the bone screw to the bone.

19. A bone fixation method according to claim 17, further comprising securing the position of the fastener relative to the bone screw using a securing mechanism.

20. A bone fixation method according to claim 17, further comprising injecting a bioactive material into an opening at one of the ends of the fastener or the bone screw.

21. A kit for pelvic bone fixation including:
    at least one bone screw each comprising:
    a first end which is threaded for engaging at least one bone in the pelvic region,
    a second end comprising a screw head, and
    at least one opening across the length of the elongate body for adjustably receiving a fastener to limit movement of the bone screw away from the engaged bone in use, wherein the at least one opening is shaped such that the position of the fastener relative to the elongate body of the bone screw can be adjusted, wherein the at least one opening provides a truncated geometry and wherein the truncated geometry is symmetrical from the center of the opening; and
    at least one of the fastener each comprising:
    an elongate body with one end adapted to engage at least one bone in the pelvic region, the elongate body being sized to be adjustably receivable in the at least one opening for interconnecting with the bone screw to limit movement of the bone screw away from the engaged bone in use, wherein the at least one bone screw and the at least one fastener have different diameters and lengths of different sizes.

22. A kit for pelvic bone fixation according to claim 21 further comprising at least one connector each being attachable to the bone screw and to an implant.

23. A kit for pelvic bone fixation according to claim 22, wherein the connector is attachable to the screw head and has a pair of upwardly extending flanges defining a slot for receiving an implant in use.

* * * * *